US005580351A

United States Patent [19]

Helgren et al.

[11] Patent Number: 5,580,351

[45] Date of Patent: Dec. 3, 1996

[54] POINTED ADAPTER FOR BLUNT ENTRY DEVICE

[75] Inventors: R. Hayes Helgren, Mundelein; David E. Kramer, Northbrook, both of Ill.

[73] Assignee: Abbott Laboratories, Abbott Park, Ill.

[21] Appl. No.: 292,678

[22] Filed: Aug. 18, 1994

Related U.S. Application Data

[63] Continuation-in-part of Ser. No. 84,666, Jun. 29, 1993, abandoned.

[51] Int. Cl.[6] .......... A61M 37/00

[52] U.S. Cl. .......... 604/411; 604/88

[58] Field of Search .......... 604/87, 88, 239, 604/240, 243, 244, 272, 411, 412, 414, 415; 128/760, 763

[56] References Cited

U.S. PATENT DOCUMENTS

| | | | |
|---|---|---|---|
| 5,342,346 | 8/1994 | Honda et al. | 604/413 |
| 5,411,499 | 5/1995 | Dudar et al. | 604/411 |

FOREIGN PATENT DOCUMENTS

| | | |
|---|---|---|
| 351643 | 1/1990 | European Pat. Off. . |

*Primary Examiner*—Corrine M. McDermott
*Attorney, Agent, or Firm*—A. Nicholas Trausch

[57] ABSTRACT

The present invention relates to a pointed adapter which enables a blunt entry device such as a blunt cannula to readily penetrate an elastomeric closure such as a conventional vial stopper. The adapter includes a breakaway collar which initially protects the adapter point from touch contamination and from accidental stick to the user.

7 Claims, 3 Drawing Sheets

POINTED ADAPTER FOR BLUNT ENTRY DEVICE

This application is Continuation-In-Part of U.S. patent application Ser. No. 08/084,666, filed Jun. 29, 1993, now abandoned.

FIELD OF THE INVENTION

The present invention relates generally to a pointed adapter which enables a blunt fluid flow device such as a blunt cannula to readily penetrate an elastomeric closure such as a conventional medical stopper. More particularly, the adapter includes a piercing element that breaks away from a collar to pierce the elastomeric closure. The collar initially positions the piercing element on the blunt device and protects the piercing element from touch contamination and/or accidental stick.

BACKGROUND OF THE INVENTION

Elastomeric closures such as stoppers and reseals are commonly used to seal various medical solution containers. For example, elastomeric stoppers are used to close small volume drug vials. Similarly elastomeric reseals are used to close the ports of flexible plastic IV solution bags.

Currently a sharp access device such as a syringe needle or a piercing pin must be used to penetrate the elastomeric closure to permit access to the solution in the sealed container. Conventionally, the elastomeric closures have thick dimensions to permit resealing after penetration and withdrawal by a sharp access device, to withstand distortion during sterilization and to prevent degradation of the solution during transit and storage. The resiliency of the elastomer and the thick dimensions thus require that a sharp access device such as a syringe needle or a piercing pin be used to penetrate the closures.

With increasing concern about diseases such as HIV and AIDS, which are carried by bodily fluids, the use of "sharp" devices in the healthcare environment is being minimized. Sharps have the potential to breach the skin barrier by an "accidental stick" and thereby potentially transmit disease. It is estimated that more than one half of the sharps currently used in hospitals are used only for fluid transfer and connection involving IV administration sets. These sharp "connectors" are being replaced by blunt cannula and pre-pierced reseals such as the Lifeshield® Blunt Cannula and the Lifeshield® Pre-pierced Reseal, both sold by Abbott Laboratories.

Currently, however, when a drug is withdrawn from a vial or added to an IV solution bag for example, a sharp needle syringe or piercing pin must be used. The majority of elastomeric closures for standard drug vials or IV solution bags currently in use cannot be readily pierced by a blunt entry devices such as the LifeShield® Blunt Cannula. Thus, many "sharp" devices remain in use.

Recent concerns about these other potential accidental sticks has led to an effort to reduce the need for healthcare providers to use sharp needles and/or pins for access to drug vials and solution bags. For example, vial adapters have been introduced to shield the healthcare provider from the sharp access devices needed to penetrate the vial stopper. The other end of the vial adapter may include a standard luer connector, or, as disclosed in U.S. Pat. No. 5,100,394 to Dunbar, et al. titled, "*Pre-Slit Injection Site*", a pre-slit septum compatible with a blunt cannula entry device. However, many healthcare workers and providers are reluctant to use the available vial adapters since the vial adapters increase the time for set-up and change-over, created additional waste material for disposal and added additional expense.

Thus, it is an object of the present invention to provide a simplified adapter that is directly usable with a blunt entry devices for fluid access through the most commonly used thick elastomeric closures such as the stoppers on standard drug vials.

It is another object of the present invention to provide a blunt cannula adapter which is economical to manufacture and easy to use.

It is another object of the present invention to provide an adapter which readily indicates that the adapter has been previously used.

Another object of the present invention is to provide an adapter which does not require undue force by the health care provider to insert the blunt entry device and adapter through an elastomeric closure, while still protecting the user from accidental stick and the adapter from touch contamination.

Other important objects of the present invention will become readily apparent from the following description and drawings.

SUMMARY OF THE INVENTION

The present invention relates to a piercing member adapted for use with a blunt entry device such as a blunt cannula to pierce a medical closure such as an elastomeric stopper or reseal. The piercing member includes a substantially hollow annular collar having a rear end adapted for an interference fit around the blunt end of the blunt cannula and a forward end adapted to abut the closure. A piercing element is concentrically positioned within the annular collar and has a pointed portion oriented forward within the forward end of the collar. An annular radial base shoulder on the piercing element defines the rear end of the pointed portion. The shoulder is adapted to abut the blunt end of the cannula. A stem portion extends to the rear front the shoulder within the rear end of the collar. An integral and frangible connection radially connects the annular collar and the piercing element. The stem portion is adapted to fit within the cannula bore. The pointed portion of the piercing member is tapered, preferably to a conical tip. The frangible connection may be frangible segments or a thin annular membrane between the conical tip and the rear end of the collar.

Other features and advantages of the present invention will become readily apparent from the following detailed description, the accompanying drawings, and the appended claims.

DETAILED DESCRIPTIONS OF THE PREFERRED EMBODIMENTS

Figures 1, 2, 2A, 3, 4:
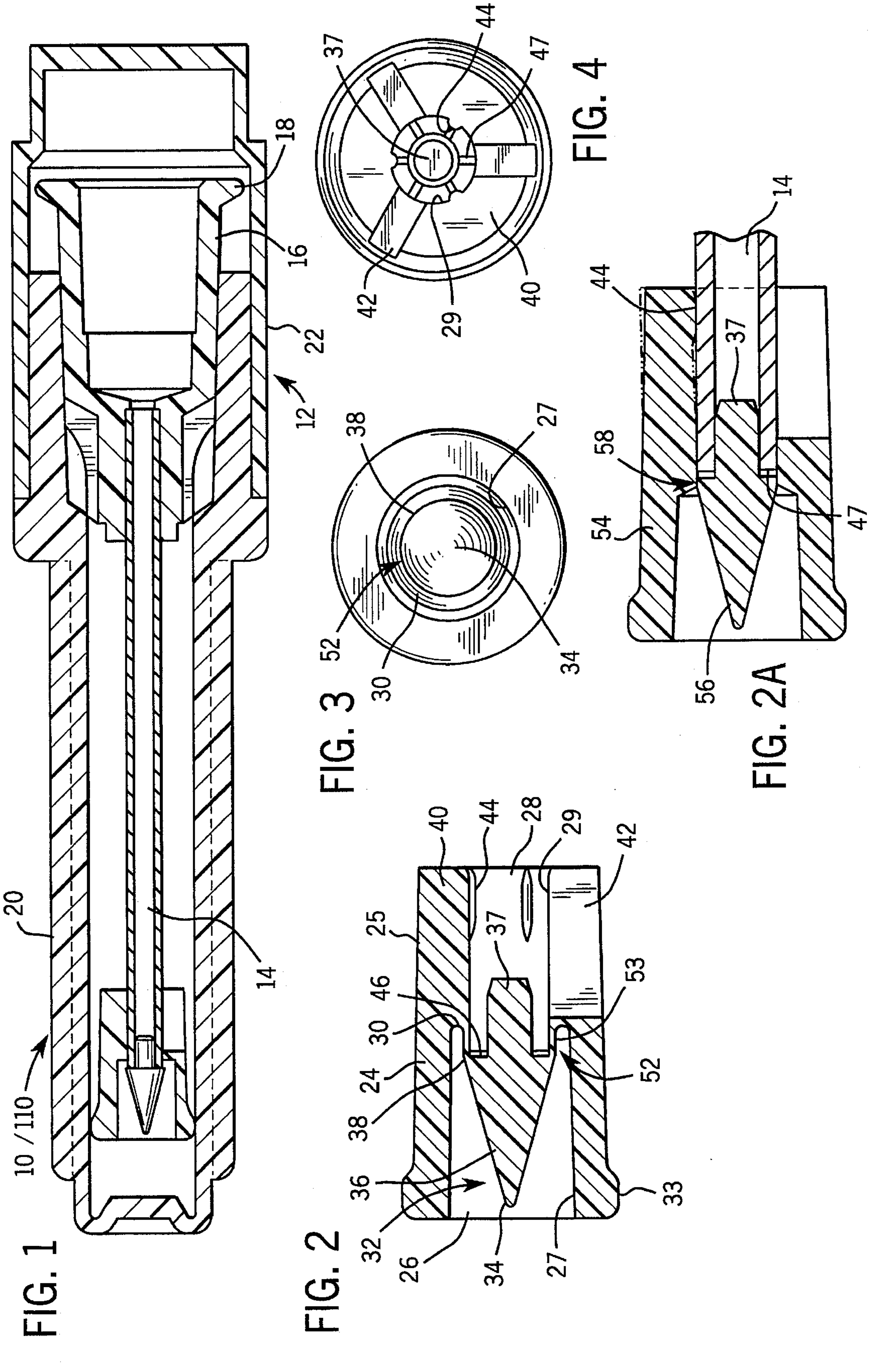
FIG. 1 is a cross-sectional view of a cannula adapter according to the present invention that is mounted on a blunt cannula and packaged in a sterile case ready for use.
FIG. 2 is an enlarged cross-sectional view of a first embodiment of a cannula adapter of FIG. 1.
FIG. 2A is a cross-sectional view of a second embodiment of an adapter similar to the adapter in FIG. 2.
FIG. 3 is a front view of the adapter embodiment of FIG. 2.
FIG. 4 is a rear view of the adapter embodiment of FIG. 2.

With reference now to FIG. 1, a sterile packaged cannula adapter 10 or 110 according to the present invention is shown assembled to a blunt access device 12 such as an Abbott LifeShield® Blunt Cannula. The blunt cannula includes a rigid (steel or plastic) cannula member 14 and a molded plastic hub 16 which securely holds the cannula. The inlet end of the hub includes a luer connector 18 for attachment to a mating luer connector on a fluid transfer device such as a standard medical syringe.

The adapter and blunt cannula are assembled, packaged and sterilized in a two-piece case which includes a bottom member 20 and top member 22. The assembled cannula adapter and blunt cannula can be sterilized using a variety of conventional sterilization processes.

Referring now to enlarged FIGS. 2–4, a first embodiment of the cannula adapter 10 will now be described. The adapter is preferably a single piece and is preferably injection molded front a medical grade plastic such as ABS (Acrylonitrile-Butadiene-Styrene). The adapter includes a substantially hollow annular collar 24 having a generally cylindrical outside surface 25 that extends axially front a front end to a rear end. As such, the collar 24 has a hollow, axially extending front portion 26 and a hollow, axially extending rear portion 28.

As best seen in FIGS. 2 and 3, the hollow front portion 26 has a inner wall surface 27, preferably cylindrical and having a first diameter. The hollow rear portion 28 has a inner wall surface 29, preferably cylindrical and having a second diameter. The diameter of the first inside wall surface 27 is greater than the diameter of the second inside wall surface 29. Thus, the collar 24 has a discontinuous annular surface or edge 30 at an intermediate position on the inner wall surfaces 27 and 29.

The front edge of the collar 24 is flared or thickened at end 33 to provide greater surface area for the adapter to contact the elastomer stopper so as to prevent the front collar portion 26 from gouging or cutting the elastomer. Also the flared end 33 is used by automated assembly machines to distinguish and directionally orient the front end of the cannula adapter 10 relative to the cannula 14 for proper automated assembly.

A detachable piercing element 32 is concentrically positioned within the annular collar 24. The piercing element includes a sharp portion 36 and a stent portion 37. The sharp portion 36 preferably has a sharp tip 34 at the front end. The first cylindrical wall surface 27 of the front portion 26 circumferentially surrounds and axially extends forward beyond the sharp portion 36. Thus, the sharp tip 34 of the piercing element 32 is initial completely within and axially recessed front the front edge 33 of the collar 24.

The sharp portion 36 of the piercing element 32 is tapered and preferably is conically tapered so as to increase in diameter from the sharp tip 34 to an outer diameter at 38. The outer diameter 38 provides a predetermined amount of clearance of the detachable piercing element 32 when detached from the collar and passing through the diameter of the first inside wall surface 27 of the front portion 26 of the collar.

Referring now to FIGS. 2 and 4, the rear portion 28 of the collar is substantially cylindrical and defines a hollow center. The inside cylindrical wall surface 29 of the rear portion 28 is longitudinally divided into a preselected number of radially flexible segments 40 by the longitudinal gaps 42. Three radially flexible segments 40 and gaps 42 are shown for example in FIG. 4. The segments 40 extend from the undivided middle portion of the annular collar 24. A small raised lip 44 is provided on the inner surface of each of the segments 40 so that a cylindrical device, such as the cannula 14 (shown in FIG. 2A for example), is subjected to an interference fit when inserted into the center of the flexible segments 40 of the rear portion of the collar 24.

A radially oriented annular shoulder 46 defines the outside part of the rear end of the tapered sharp portion 36 of the piercing element 32. Small fluid passageways 47 best seen in FIGS. 2A and 4 are provided on the annular shoulder 46 to allow fluid (i.e., air or solution) to be communicated from the outside of the cannula 14 through the passageways 47 and into the bore of the cannula, as will be described later. The cylindrical stem portion 37 concentrically extends rearward from the center of the annular shoulder 46. The shoulder 46 and the stem portion 37 are sized to fit against the blunt end and in the bore, respectively, of the cannula 14.

A circumferential connection 52 connects the cylindrical collar 24 with the piercing element 32. In the first embodiment of FIGS. 2–4, the connection at 52 is integral and frangible. Preferably the frangible connection is a radially thin circumferential sleeve 53 integrally molded between the outer diameter 38 of the piercing element 32 and the discontinuous annular edge 30 of the inner surface of cylindrical wall surfaces 27 and 29.

In a second embodiment of the invention as shown in FIG. 2A, an alternate collar 54 is manufactured as a separate piece. An alternate piercing element 56 is also manufactured separately. The two pieces 54 and 56 are then assembled and joined together at the mechanical connection 58 by force, friction, adhesive, or any other suitable joining method. The connection 58 is detachable.

Referring now to FIGS. 9–12, the preferred embodiment of the cannula adapter 110 will now be described. The adapter is preferably a single piece and is preferably injection molded from a medical grade plastic such as ABS (Acrylonitrile-Butadiene-Styrene). The preferred adapter 110 includes a substantially hollow annular collar 124 having a generally cylindrical outside surface 125 that extends axially from a front end to a rear end. As such, the collar 124 has a hollow, axially extending front portion 126 and a hollow, axially extending rear portion 128.

Figures 9, 9A, 10, 11, 12, 13, 13A:
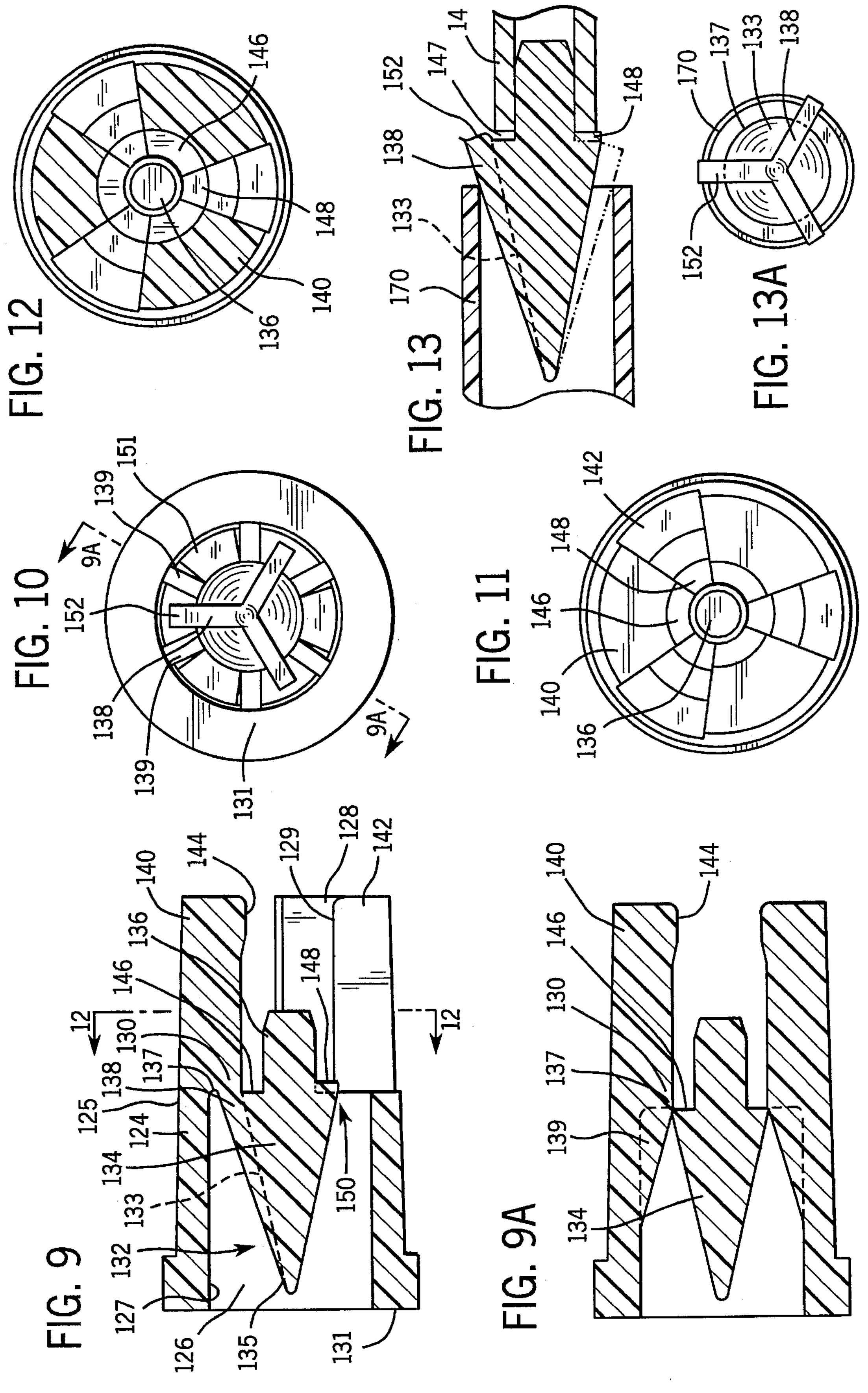
FIG. 9 is a cross-sectional view of the preferred embodiment of the cannula adapter of FIG. 1.
FIG. 9A is another cross-sectional view of the embodiment of FIG. 9 at section 9A—9A in FIG. 10.
FIG. 10 is a front view of the adapter embodiment of FIG. 9.
FIG. 11 is a rear view of the adapter embodiment of FIG. 9.
FIG. 12 is a sectional view of the adapter embodiment of FIG. 9 at section 12—12 in FIG. 9.
FIG. 13 shows the preferred embodiment of the piercing element of the invention in a standard gauge catheter tubing.
FIG. 13A is a rear view of FIG. 13.

As best seen in FIGS. 9 and 10, the forward portion 126 has a inner wall surface 127, preferably cylindrical and having a first diameter. The rear portion 128 has a inner wall surface 129, preferably cylindrical and having a second diameter. The diameter of the first inside wall surface 127 is greater than the diameter of the second inside wall surface 129. Thus, the collar 124 has a transition portion 130 at an intermediate position on the inner wall surfaces 127 and 129.

The front portion 126 of the collar 124 is flared or thickened at end 131 to provide greater surface area for the adapter to contact the elastomer surface to be pierced so as to prevent the front collar portion 126 from gouging or cutting the elastomer. Also the flared end 131 is used by automated assembly machines to distinguish and directionally orient the front end of the cannula adapter 110 relative to the cannula 14 for proper automated assembly.

A detachable piercing element 132 is concentrically positioned within the annular collar 124. The piercing element includes a sharp portion 134 and a stem portion 136. The first inside wall surface 127 of the front portion 126 of the collar circumferentially surrounds and axially extends forward beyond the sharp portion 134. Thus, the sharp portion 134 of the piercing element 132 is initially completely within and axially recessed from the front or leading edge 131 of the collar 124.

The sharp portion 134 of the piercing element 132 has a tapered surface 133 that preferably is conically tapered so as to increase in diameter from a sharp tip 135 to an outer diameter at 137. At the outer diameter 137, the tapered surface 133 of the piercing element minimally and circumferentially joins the transition portion 130 of the surfaces 127 and 129.

The sharp portion 134 also includes a plurality of longitudinal ribs 138 extending along the tapered surface 133 from the sharp tip 135 to the outer diameter 137 as shown in FIGS. 9 and 10. Three ribs are shown in FIG. 10. The ribs 138 also join the transition portion 130 of the collar 124. As best seen in FIG. 10, the ribs provide a solid yet frangible connection at 150 to the collar 124. The portion of the ribs 138 that extend beyond the outer diameter 137 have a predetermined amount of clearance with the first inner wall surface 127 of the collar that allows the detached piercing element 132 to pass through the inside wall surface 127 of the front portion 126 of the collar.

The inner wall surface 127 of the hollow front portion also includes pairs of longitudinal gussets or supports 139 that oppositely flank each rib 138 as shown in FIGS. 9A and 10. The gussets strengthen the transition portion 130 and the hollow front wall portion 126 of the collar 124. The ribs 138 and gussets 139 are separated from each other. An open area 151 is defined between the collar 124 and the piercing element 132.

As seen in FIG. 13, the ribs 138 also prevent the detached piercing element 132 from passing through or occluding a standard gauge catheter tubing 170. If the detached piercing element does enter the tubing, fluid can still flow through the open spaces between each pair of ribs at the outer diameter 137 on the tapered conical surface 133 of the piercing element 132 as shown in FIG. 13A.

Referring now to FIGS. 9 and 11, the rear portion 128 of the collar 124 is substantially cylindrical and defines a hollow center. The inside cylindrical wall surface 129 of the rear portion 128 is longitudinally divided into a preselected number of radially flexible segments 140 by the longitudinal gaps 142. Three radially flexible segments 140 and gaps 142 are shown for example in FIG. 11. The segments 140 extend from the undivided portion of the annular collar 124. A small raised lip 144 is provided on the inner surface of each of the segments 140 so that a cylindrical device, such as the blunt cannula (shown in FIG. 2A for example), is subjected to an interference fit when inserted into the center of the flexible segments of the rear portion 128.

A radially oriented base shoulder 146 defines the outside annular part of the rear end of the sharp portion 134 of the piercing element 132. Small axially extending pads 148 are provided on the face of the base shoulder 146 to create offset spaces 147. As shown in FIG. 13, the spaces 147 allow fluid (i.e., air and/or solution) to communicate from the outside of the cannula 14 through the offset spaces 147 to the bore of the cannula. Thus, for example, air can be drawn into a syringe with the adapter in place in the bore of the blunt cannula.

The cylindrical stent portion 136 concentrically extends rearward from the base shoulder 146. The annular base shoulder 146 is sized to fit against the blunt end of the cannula 14. The cylindrical stem portion 136 is sized to loosely fit in the bore of the cannula.

Thus, a frangible connection 150 connects the hollow cylindrical collar 124 with the piercing element 132. Radially spaced frangible segments 152 that extend front the longitudinal ribs 138, beyond the outer diameter 137, provides the frangible connection. The frangible segments of the preferred embodiment provide advantages over the first embodiment of FIGS. 2–4. In the first embodiment only a radially thin annular circumferential sleeve 53 was molded between the outer diameter 38 of the piercing element 32 and the discontinuous edge 30 of the inner surface of cylindrical walls 27 and 29. The segments 152 of the preferred embodiment of FIGS. 9–12 provides stronger support for the frangible connection and facilitates better flow of material during the manufacturing process. The thicker area at segments 152 are used as gates for material flow to the stem portion 136 and the sharp portion 134 during injection molding.

Referring now to FIGS. 5–8, a typical procedure for using an assembled syringe, blunt cannula and piercing adapter 10 or 110 will now be described. In FIG. 5A the covered and sterile blunt cannula 12 and adapter 110 of FIG. 1 has been attached to the mating luer connector of a standard syringe 60 and is ready for use.

Figures 5, 5A, 5B, 6, 7, 8:
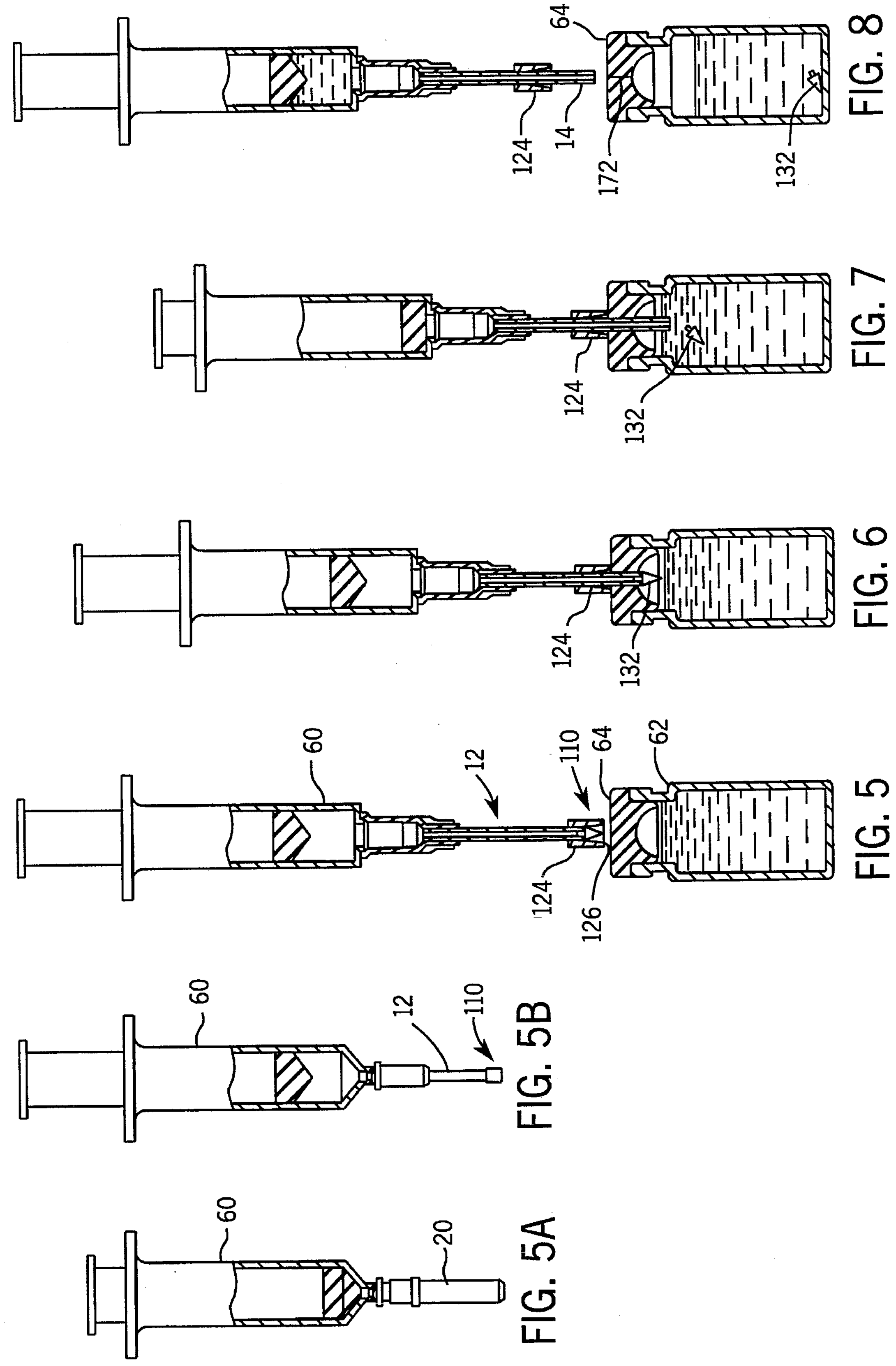
FIG. 5 is a cross-sectional view of the syringe, blunt cannula, and the cannula adapter of FIG. 5B abutting an elastomeric stopper of a conventional drug vial.
FIG. 5A is a schematic view of a syringe, blunt cannula, and the cannula adapter of the present invention with the adapter enclosed in a cover prior to use.
FIG. 5B is a schematic view of the syringe, blunt cannula, and the cannula adapter of FIG. 5A with the cover removed and with air drawn into the syringe.
FIG. 6 is a cross-sectional view of the syringe, blunt cannula and cannula adapter of FIG. 5B as the adapter pierces the elastomeric stopper.
FIG. 7 is a cross-sectional view of the syringe, blunt cannula and cannula adapter of FIG. 6 after the piercing element of the adapter has disengaged from the blunt cannula and air has been injected into the vial.
FIG. 8 is a cross-sectional view of the syringe, blunt cannula and cannula adapter of FIG. 7 after solution has been drawn into the syringe and the blunt cannula has been withdrawn from the drug vial.

In FIG. 5B the case bottom 20 is removed so as to expose the blunt cannula 12 and the adapter 110. At this point in time, if the prepackaged and assembled adapter will not be utilized, the adapter 110 can be removed from the blunt cannula 14 merely by gripping the adapter at the collar 124, for example, and pulling the adapter 110 axially off the cannula 14. With the adapter removed, the syringe cannula remains sterile and ready for use as a conventional blunt cannula syringe.

However, if the healthcare provider needs access to a solution in a medical container such as the stoppered vial, the adapter 110 of the present invention is left in place and is utilized. As seen in FIG. 5B, the syringe plunger is pulled back slightly, as is common practice. This draws air into the syringe chamber for the purpose of later pressurizing the vial. The offset spaces 147 allow air to be drawn into the bore of the cannula through the attached adapter.

In FIG. 5, the syringe and adapter is positioned in abutting contact with the elastomeric stopper 64 of a drug vial 62 so that the forward end 126 of the collar is in contact with the target area of the stopper.

In FIG. 6, axial force of approximately 4 lbs., is applied to the syringe so that the piercing element 132 breaks away from the collar 124 at the frangible connection 150. The piercing element 132 now allows the blunt cannula 12 to penetrate through the stopper with the continued application of approximately 4 lbs. of force. This force is significantly less than the force required, if at all possible, to penetrate a standard elastomeric stopper using only a blunt cannula.

Referring now to FIG. 7, once the cannula has completely penetrated the stopper, the vial is pressurized by moving the syringe plunger forward. If the stem portion of the piercing element 132 has not yet disengaged from the bore of the cannula, the pressurizing fluid will push the stent front the cannula as shown. The solution can then be withdrawn from the vial by using the syringe in the normal manner. It is also possible to draw small amounts of fluid into the syringe chamber to pressurize the vial via the offset spaces 147 on the face of the annular shoulder 146 with the stem still in place in the cannula bore.

Referring now to FIG. 8, when the syringe is filled as required, the cannula 14 is extracted front the stopper. The detached piercing element 132 remains inside the vial and the breakaway collar 124 remains on the cannula 14 due to the interference fit of the flexible segments 140. Thus, the syringe is now configured as a blunt cannula syringe and can safely be used in conjunction with suitable reseal connections such as for example the Abbott LifeShield® Prepierced Reseal. Additionally, the same blunt cannula or a new blunt cannula can re-enter the vial stopper 64 through the resealed access hole 172 that was initially pierced by the detached piercing element of the cannula adapter 110.

The present invention has many advantages. The adapter 110 allows a blunt cannula to easily pierce a stopper with the addition of the piercing element 132 while safely preventing accidental stick by the piercing element 132 due to the recessed position of the sharp portion in the breakaway collar 124. Since the blunt cannula comes packaged with the piercing adapter 110 already attached, the healthcare user is more efficient because the adapter does not have to be unpackaged and attached by the user. Also, risk of contamination to the cannula is reduced because the adapter is already attached. Furthermore, the piercing adapter 110 can be readily removed without compromising the sterility of the blunt cannula because only the collar 124 of the adapter is touched during removal.

Another advantage of the present invention is that the adapter is economical to manufacture, especially in the preferred integral embodiment since the adapter can be molded in one piece and is easily machine assembled to the blunt cannula prior to packaging and sterilization. Also, since the adapter is also assembled and packaged with the blunt cannula, no additional disposal of waste packaging materials is required.

Another use of the adapter of the present invention is with blunt entry devices used for removing sample fluids, such as blood, from specimen vials. For example, the adapter of the present invention could be used with the Vacutainer blood sampling system sold by Becton-Dickinson.

From the foregoing, it will be observed that numerous modifications and variations can be affected without departing from the true spirit and scope of the novel concept of the present invention. It is to be understood that no limitation with respect to the specific embodiment is intended or should be inferred. Disclosures intended to be covered by the appended claims and all such modifications as fall within the scope of the claims.

We claim:

1. A piercing member constructed and arranged for use with an associated blunt end of a hollow cannula to pierce an elastomeric closure, the piercing member comprising:

an annular collar having a generally cylindrical outside surface axially extending from a front end to a rear end, the collar having a hollow front portion having a first inside cylindrical wall surface with a first diameter, the front portion constructed and arranged for axially abutting the closure, and a hollow rear portion having a second inside cylindrical wall surface with a second diameter, the rear portion constructed and arranged for an interference fit around the cannula, the diameter of the first inside wall surface being greater than the diameter of the second inside wall surface;

a detachable piercing element concentrically positioned within the annular collar and having a sharp portion extending axially forward within the front portion of the collar and a stent portion extending to the rear within the rear portion of the collar; and means for detachably connecting the piercing element to the collar wherein the connection means is a frangible connection having an annular integral connection extending between the detachable piercing element and the second inside wall surface of the rear portion of the collar and wherein the piercing element includes an axially forward extending tapered sharp portion, a cylindrical stem portion constructed and arranged to fit within a blunt end of a cannula and a transition portion at the juncture of the sharp portion and the stem portion wherein the transition portion includes spaces for fluid flow communication between an outside of a cannula and a bore of a cannula; and wherein the sharp portion of the piercing element has a conical surface that increases in diameter front a tip point to an outer diameter on the transition portion and includes a plurality of longitudinal ribs on the conical surface that are frangibly connected to the annular collar at the transition portion.

2. A piercing adapter constructed and arranged for use with an associated blunt end of a hollow bore cannula to pierce an elastomeric closure, the piercing adapter comprising:

an annular collar having a generally cylindrical outside surface and a hollow inside surface, both the outside and inside surfaces of the collar extending from a front end to a rear end, the inside surface including a rear portion having a second inside diameter and a radially inward raised lip at the rear end, the lip having an interference fit around an associated blunt end of a cannula, the inside surface also including a front portion having a first inside diameter, the front end of the collar constructed and arranged to abut an elastomeric closure, the inside surface of the collar also including a discontinuous transition portion between the front and rear portions, wherein the first inside diameter is greater than the second inside diameter;

a detachable piercing element concentrically positioned within the annular collar and having a sharp conical portion extending axially forward within the front portion of the collar and a stem portion extending axially toward the rear end within the rear portion of the collar; and detachable means for connecting the piercing element to the annular collar wherein the stem portion is cylindrical and constructed to fit loosely within a bore of an associated cannula and the piercing element further includes a radial base shoulder at a juncture of the conical portion and the stem portion with a plurality of axially extending pads on the radial base shoulder to provide an axial offset space between the adapter and a blunt end of an associated cannula.

3. The piercing adapter of claim 2 wherein the piercing element increases in diameter from a conical point to an outer diameter at the radial base shoulder.

4. The piercing adapter of claim 3 wherein the outer diameter at the radial base shoulder is greater than a blunt end of an associated cannula.

5. The piercing adapter of claim 4 wherein the detachable means is a frangible connection.

6. The piercing adapter of claim 5 wherein the frangible connection is a thin annular sleeve between the outer diameter of the piercing element and the rear portion of the collar.

7. The piercing adapter of claim 5 further including a plurality of longitudinal ribs on the portion that are frangibly connected to the annular collar at the radial base shoulder.

* * * * *

UNITED STATES PATENT AND TRADEMARK OFFICE

CERTIFICATE OF CORRECTION

PATENT NO. : 5,580,351

DATED : December 3, 1996

INVENTOR(S) : Helgren, et. Al.

It is certified that error appears in the above-indentified patent and that said Letters Patent is hereby corrected as shown below:

Column 8, line 30, change "stent" to --stem--.

Column 8, line 46, change "front" to --from--.

Signed and Sealed this

First Day of April, 1997

Attest:

BRUCE LEHMAN

*Attesting Officer*

*Commissioner of Patents and Trademarks*